（12）United States Patent
Carson et al.

(10) Patent No.: US 8,699,030 B2
(45) Date of Patent: *Apr. 15, 2014

(54) APPARATUS FOR SENSING OF CHLORINE DIOXIDE

(75) Inventors: William W. Carson, Hopkinton, MA (US); Paul Sabin, Needham, MA (US); Thomas J. Dee, Holliston, MA (US)

(73) Assignee: TBS Technologies, LLC, Holliston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/601,288

(22) Filed: Aug. 31, 2012

(65) Prior Publication Data

US 2013/0188189 A1    Jul. 25, 2013

Related U.S. Application Data

(63) Continuation of application No. 12/975,396, filed on Dec. 22, 2010, now Pat. No. 8,284,403, which is a continuation of application No. PCT/US2009/049924, filed on Jul. 8, 2009.

(60) Provisional application No. 61/134,245, filed on Jul. 8, 2008.

(51) Int. Cl.
*G01N 21/00* (2006.01)

(52) U.S. Cl.
USPC .......................................................... 356/437

(58) Field of Classification Search
USPC .......................................................... 356/437
See application file for complete search history.

(56) References Cited

U.S. PATENT DOCUMENTS

| 3,808,436 | A | 4/1974 | Risgin et al. |
| 4,311,485 | A | 1/1982 | Saltzman et al. |
| 5,030,420 | A | 7/1991 | Bacon et al. |
| 5,246,868 | A | 9/1993 | Busch et al. |
| 6,304,327 | B1 | 10/2001 | Campbell et al. |
| 6,844,554 | B2 * | 1/2005 | Karlsson ................. 250/339.13 |
| 6,853,452 | B1 * | 2/2005 | Laufer ........................ 356/436 |
| 7,288,770 | B2 | 10/2007 | Gamiles et al. |
| 7,301,639 | B1 | 11/2007 | Kebabian et al. |
| 2007/0113686 | A1 | 5/2007 | Desrochers et al. |

OTHER PUBLICATIONS

International Preliminary Report on Patentability for International Application No. PCT/US09/049924 (Jan. 20, 2011).
International Search Report for International Application No. PCT/US09/049924 (Aug. 27, 2009).
Written Opinion for International Application No. PCT/US09/049924 (Aug. 27, 2009).

* cited by examiner

*Primary Examiner* — Tu Nguyen
(74) *Attorney, Agent, or Firm* — McCarter & English, LLP; Jonathan M. Sparks; Colleen H. Witherell

(57) ABSTRACT

The instant invention provides apparatuses for measuring the level or concentration of chlorine dioxide gas in a sample and methods of using the same. One aspect of the invention provides an apparatus for measuring a concentration of a chlorine dioxide gas in a sample. The apparatus includes a light emitting diode (LED), a light sensor, and a flow path between the LED and the light sensor, and a filter configured to remove chlorine dioxide from a reference stream. The flow path is capable of containing a sample. The sensor is capable of measuring the level of chlorine dioxide in the sample and the reference stream.

16 Claims, 10 Drawing Sheets

Inside of sensor apparatus

Sensor apparatus with cover

APPARATUS FOR SENSING OF CHLORINE DIOXIDE

RELATED APPLICATIONS

This application is a continuation of U.S. application Ser. No. 12/975,396, filed on Dec. 22, 2010, allowed, which is a continuation of International Application No. PCT/US2009/049924, filed Jul. 8, 2009, which claims the benefit of U.S. Provisional Application 61/134,245 filed on Jul. 8, 2008. The entire contents of the aforementioned applications are hereby incorporated by reference.

FIELD OF THE INVENTION

The present invention relates to methods and apparatuses for the sensing and delivery of chlorine dioxide, e.g., gaseous chlorine dioxide.

BACKGROUND OF THE INVENTION

Chlorine dioxide was discovered in the early 1800's, and was adopted by commerce in the United States in the 1940's. Chlorine dioxide has been called the ideal biocide and the ability of chlorine dioxide to reduce or eliminate viable microbes, e.g., bacteria, viruses, fungi, mold spores, algae and protozoa, is well-documented and well known. See, for example, Franklin, C. L. et al. (1991) *Am Vet Med Assoc* 198:1625-30; Korich K. G., et al. (1990) *Appl Environ Microbiol.* 56:1423-8; Boddie et al. (2000) *J Dairy Sci.* 83:2975-9; Lee et al. (2004) *J Food Prot.* 67:1371-6; Han et al. (2003) *J Environ Health* 66:16-21; Sy et al. (2005) *J Food Prot.* 68:1176-87; and LeChevallier M. W. et al. (1988) *Appl Environ Microbiol.* 54:2492-9.

Chlorine dioxide inactivates microorganisms by oxidizing key components of a micro-organism's membrane proteins that are vital to the membrane's structure and function. Also, the oxidizing reaction that causes microorganism inactivation does not form trihalomethanes (THMs) or haloacetic acids (HAAs).

Approvals and registrations for use of chlorine dioxide in a wide variety of applications have been granted by the EPA, FDA and USDA, and such approvals and registrations have led to an increasing adoption of the use of chlorine dioxide.

There are many reasons for the ongoing expansion of chlorine dioxide use including its effectiveness against microorganisms.

Accordingly, with the increased use of chlorine dioxide the need exists for sensing chlorine dioxide concentration in a sample to determine and to validate efficacy of performance with a proscribed concentration of chlorine dioxide and/or to determine when a treated environment is safe.

SUMMARY OF THE INVENTION

The instant invention provides apparatus and methods for sensing the amount or levels of chlorine dioxide gas in a sample.

In one embodiment, the invention provides apparatuses for measuring a concentration of a chlorine dioxide gas in a sample, comprising a light emitting diode (LED), a light sensor, and a flow path between the LED and the light sensor, the flow path capable of containing a sample, wherein the sensor is capable of measuring the level of chlorine dioxide in a sample and a reference measurement.

In one embodiment, the apparatus further comprises one or more filters, wherein the filters are used to remove the chlorine dioxide gas from a sample to obtain the reference measurement.

In another embodiment, the apparatus further comprises a second LED, light sensor and flow path for determining the reference measurement.

In a specific embodiment, the sample is obtained from a location that has not been treated with chlorine dioxide, i.e., when determining the level in a reference measurement.

In another embodiment, the sample is not measured until the reference measurement is less than about 10 ppm chlorine dioxide.

In another embodiment, the sensor and/or LED is thermostated. In another embodiment, the sensor is heated, for example, to prevent condensation.

In another embodiment, the LED generates a narrow wavelength band. In a specific embodiment, the wavelength band is narrower than the absorbance band of chlorine dioxide. In a specific embodiment, the narrow wavelength band is in the UV, for example near an absorption peak of chlorine dioxide.

In one embodiment, the light sensor is a photodiode. In a specific embodiment, the photodiode sensitivity is matched to the LED. In one embodiment, the apparatus further comprises a filter to select a wavelength of light matched to the LED.

In another embodiment, the apparatus further comprises an air moving device, e.g., a fan or a pump.

In one embodiment, the apparatus further comprises an inlet and an outlet port for the target sample. In one embodiment, the filter is at the inlet. In a specific embodiment, the filter is an activated carbon filter.

In another embodiment, the filter further comprises a filter at the outlet. In one embodiment, the filter is suitable for filtering acids or hydrogen chloride gas.

In exemplary embodiments, the path lengths are 1, 2, 3, 4, 5, 6, 7, 8, 9, 10, 11, 12 or more inches in length.

In another embodiment, the light attenuation is less than 10%.

In another embodiment, the path between the sensor and the detector includes one or more minors. In a specific embodiment, the one or more minors are curved. In another embodiment, the mirrors are for focusing the light source on the light sensor. In a specific embodiment, the mirrors are moveable.

In another embodiment, the apparatuses further comprise two or more paths used for sensing different concentration levels or for reference measurements.

In another embodiment, the apparatuses further comprise one or more lenses for focusing the light on the detector.

In another embodiment, the apparatuses further comprise one or more signal amplifiers.

In another embodiment, the apparatuses further comprise a recorder or indicator, e.g., a recorder or indicator having a wireless connection to a recorder or display.

In one embodiment, the apparatus further comprises a chlorine dioxide generating apparatus.

In another embodiment, the invention provides apparatuses for measuring a concentration of a chlorine dioxide gas in a sample, comprising a first sensor for measuring the level of chlorine dioxide gas in a sample, and a second sensor for measuring the level of chlorine dioxide gas in a sample; wherein each sensor comprises: a light emitting diode (LED), a light sensor, and a flow path between the LED and the light sensor, the flow path capable of containing a sample, and wherein the second sensor measures the levels of chlorine dioxide gas in sample after the first sensor determines that the level of chlorine dioxide gas in a sample is less than about 15 ppm; and wherein second sensor also measures a reference measurement.

In one embodiment, the second sensor further comprises one or more filters to remove chlorine dioxide gas from a sample prior to measuring the reference measurement.

In another embodiment, the sample is obtained from a location that has not been treated with chlorine dioxide.

In another embodiment, the sensors and/or LEDs are thermostated. In another embodiment, the sensors are heated, for example, to prevent condensation.

In another embodiment, the LEDs generate a narrow wavelength band. In a specific embodiment, the wavelength band is narrower than the absorbance band of chlorine dioxide. In a specific embodiment, the narrow wavelength band is in the UV, for example near an absorption peak of chlorine dioxide.

In one embodiment, the light sensor is a photodiode. In a specific embodiment, the photodiode sensitivity is matched to the LED. In one embodiment, the apparatus further comprises a filter to select a wavelength of light matched to the LED.

In another embodiment, the apparatus further comprises an air moving device, e.g., a fan or a pump.

In one embodiment, the apparatus further comprises an inlet and an outlet port for the target sample. In one embodiment, the filter is at the inlet. In a specific embodiment, the filter is an activated carbon filter.

In another embodiment, the filter further comprises a filter at the outlet. In one embodiment, the filter is suitable for filtering acids or hydrogen chloride gas.

In exemplary embodiments, the path lengths are 1, 2, 3, 4, 5, 6, 7, 8, 9, 10, 11, 12 or more inches in length.

In another embodiment, the light attenuation is less than 10%.

In another embodiment, the path between the sensor and the detector includes one or more minors. In a specific embodiment, the one or more minors are curved. In another embodiment, the mirrors are for focusing the light source on the light sensor. In a specific embodiment, the mirrors are mirrors are moveable.

In another embodiment, the apparatuses further comprise two or more paths used for sensing different concentration levels or for reference measurements.

In another embodiment, the apparatuses further comprise one or more lenses for focusing the light on the detector.

The invention also provides methods for determining the amount of level of chlorine dioxide gas in a sample using the chlorine dioxide sensor apparatuses described herein.

DETAILED DESCRIPTION

The instant invention provides methods and apparatus for measuring the amount or concentration of chlorine dioxide gas in a sample. In specific embodiments, the apparatus also obtains a reference measurement of the amount or concentration of chlorine dioxide gas in a reference sample.

Figure 1:
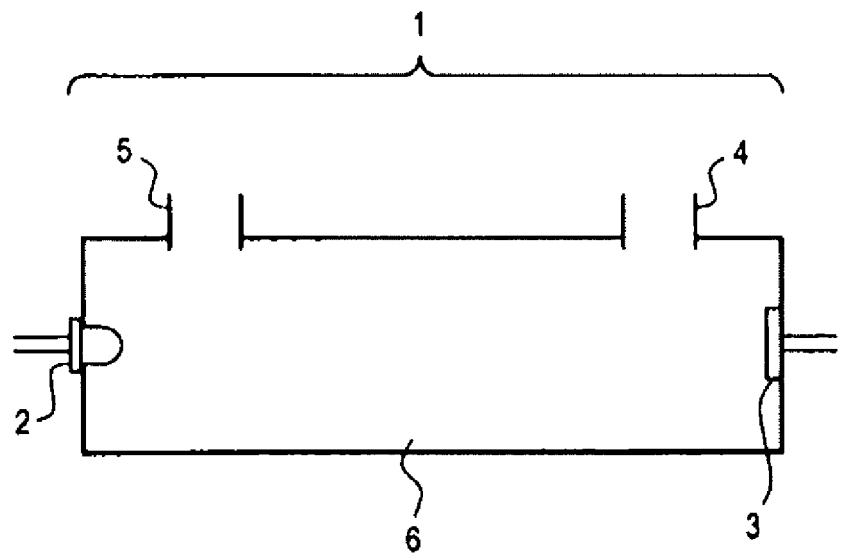
FIG. 1 depicts a chlorine dioxide sensor apparatus of the invention.

In reference to FIG. 1, the invention provides a chlorine dioxide sensor apparatus 1, comprising inlet 4, outlet 5, and light emitting diode (LED) 2 separated from photodetector 3 by flow path 6. Flow path 6 is of sufficient volume to contain a sample of gas, e.g., gas comprising chlorine dioxide gas. In one embodiment of the invention LED 2 is set up opposite a photodiode 3 so that the sample flows between the LED and the photodiode.

Figure 2:
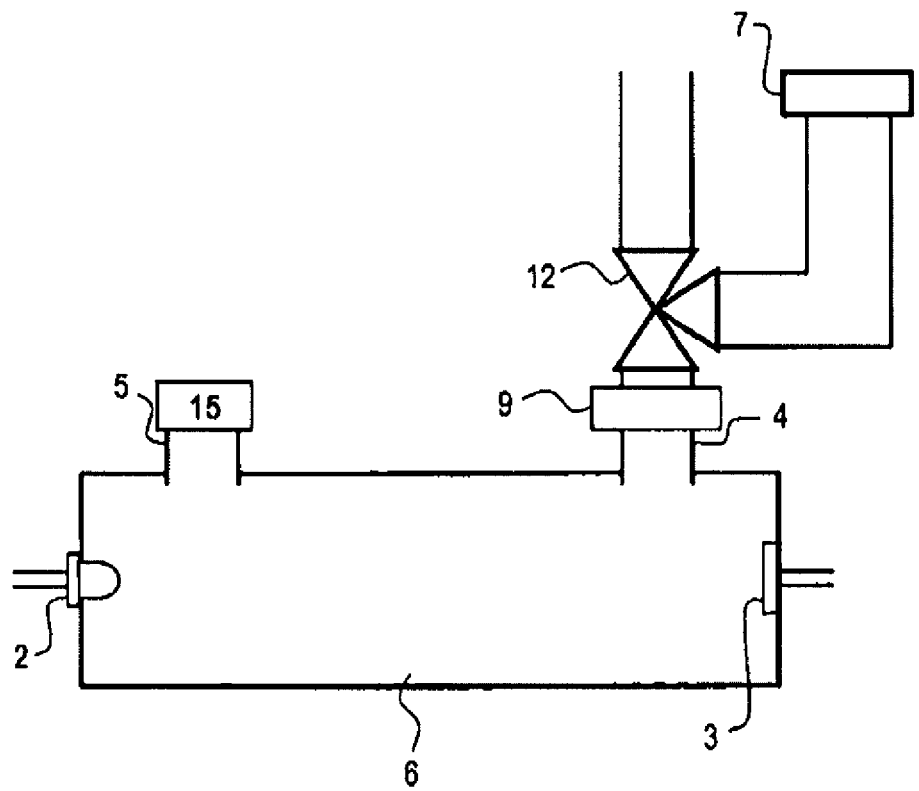
FIG. 2 depicts a chlorine dioxide sensor apparatus comprising a filter and an air moving device.

In reference to FIG. 2, in certain embodiments, the invention provides a chlorine dioxide sensor apparatus as in FIG. 1, and further comprising filter 7, air moving device 9 and valve 12. Valve 12 functions to control the location that the sample is collected from prior to entry into flow path 6. Air moving device 9 assists in moving the sample through flow path 6. In exemplary embodiments, air moving device 9 is a fan.

Figure 3:
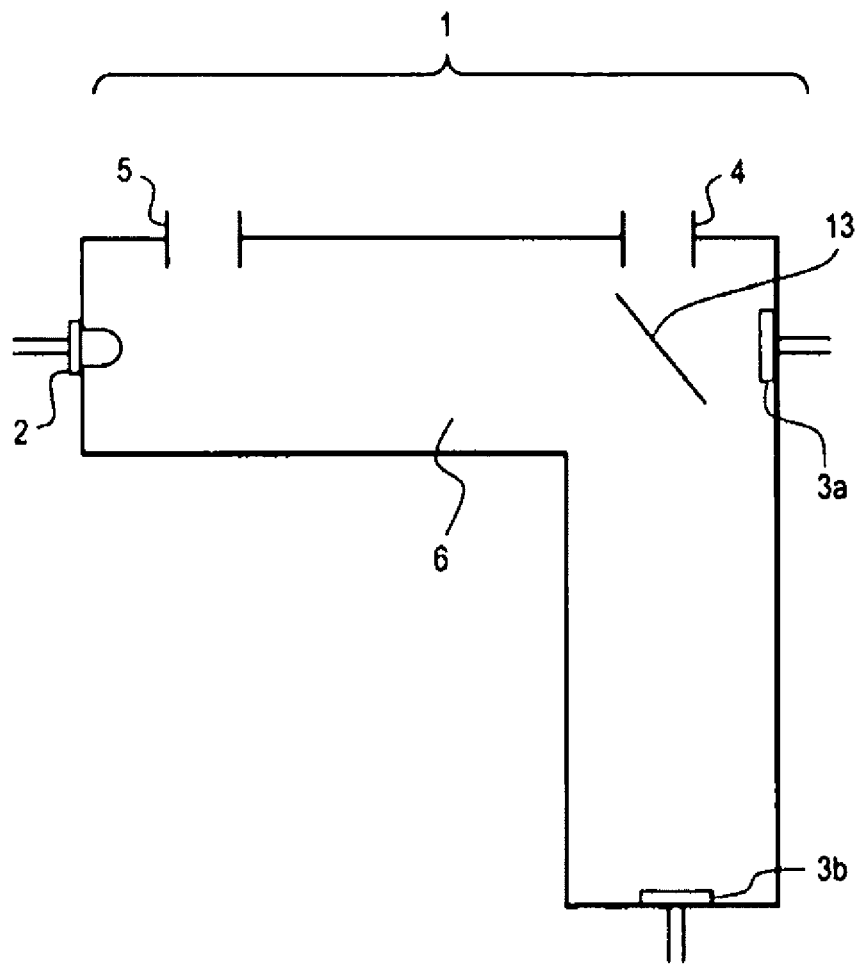
FIG. 3 depicts a chlorine dioxide sensor apparatus with two path lengths.

FIG. 3 depicts an alternative geometry of the chlorine dioxide sensor apparatus wherein apparatus comprises a beam splitter 13. This embodiment comprises two photodetectors 3 and a geometry such that a portion of the light from LED 2 is directed to photodetector 3a and a portion is directed to photodetector 3b.

Figure 4A:
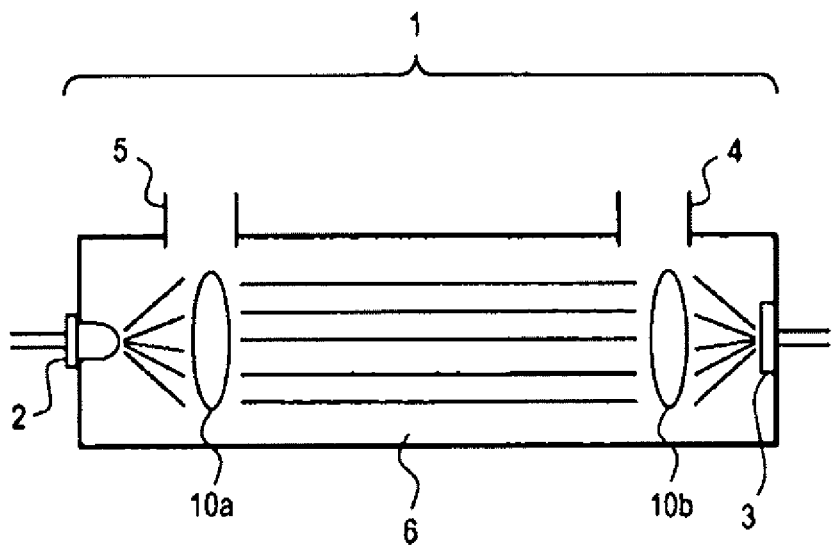
FIG. 4a depicts a chlorine dioxide sensor apparatus with a lens.
Figure 4B:
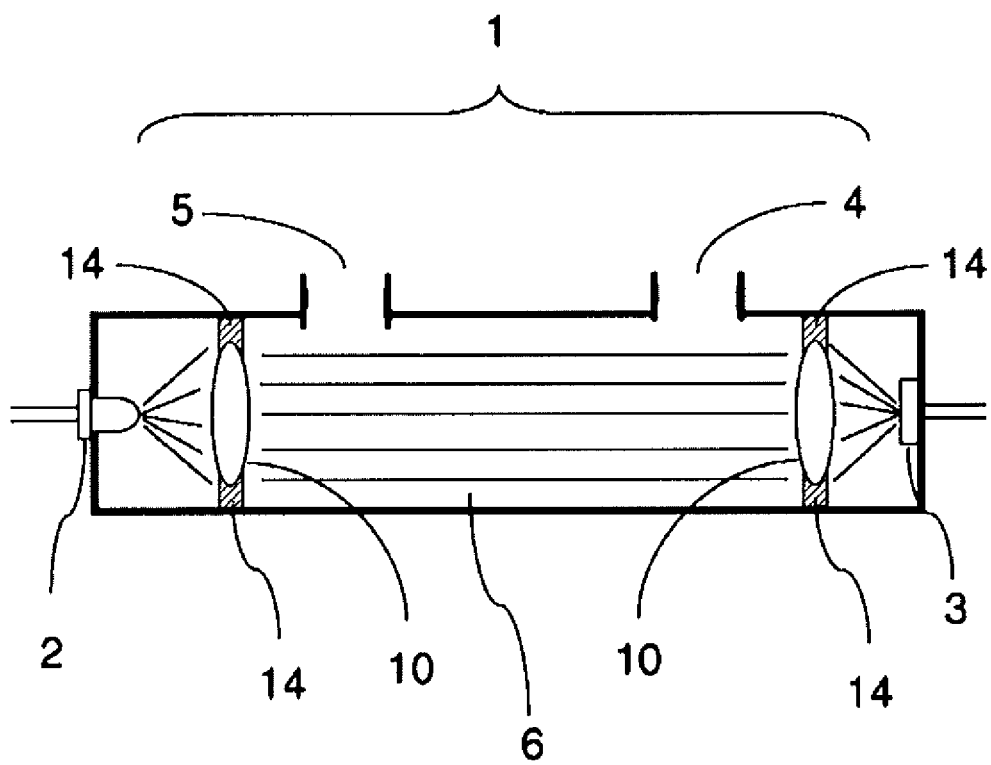
FIG. 4b depicts the chlorine dioxide sensor apparatus as in FIG. 4a further comprising gas tight seals.

FIG. 4 depicts an additional element of chlorine dioxide sensor apparatus 1. Specifically, FIG. 4 depicts lens 10a and lens 10b placed in path length 6 proximal to LED 2 and photodetector 3, respectively. FIG. 4b further depicts gas tight seals 14 around lens 10a and 10b.

Figure 5:
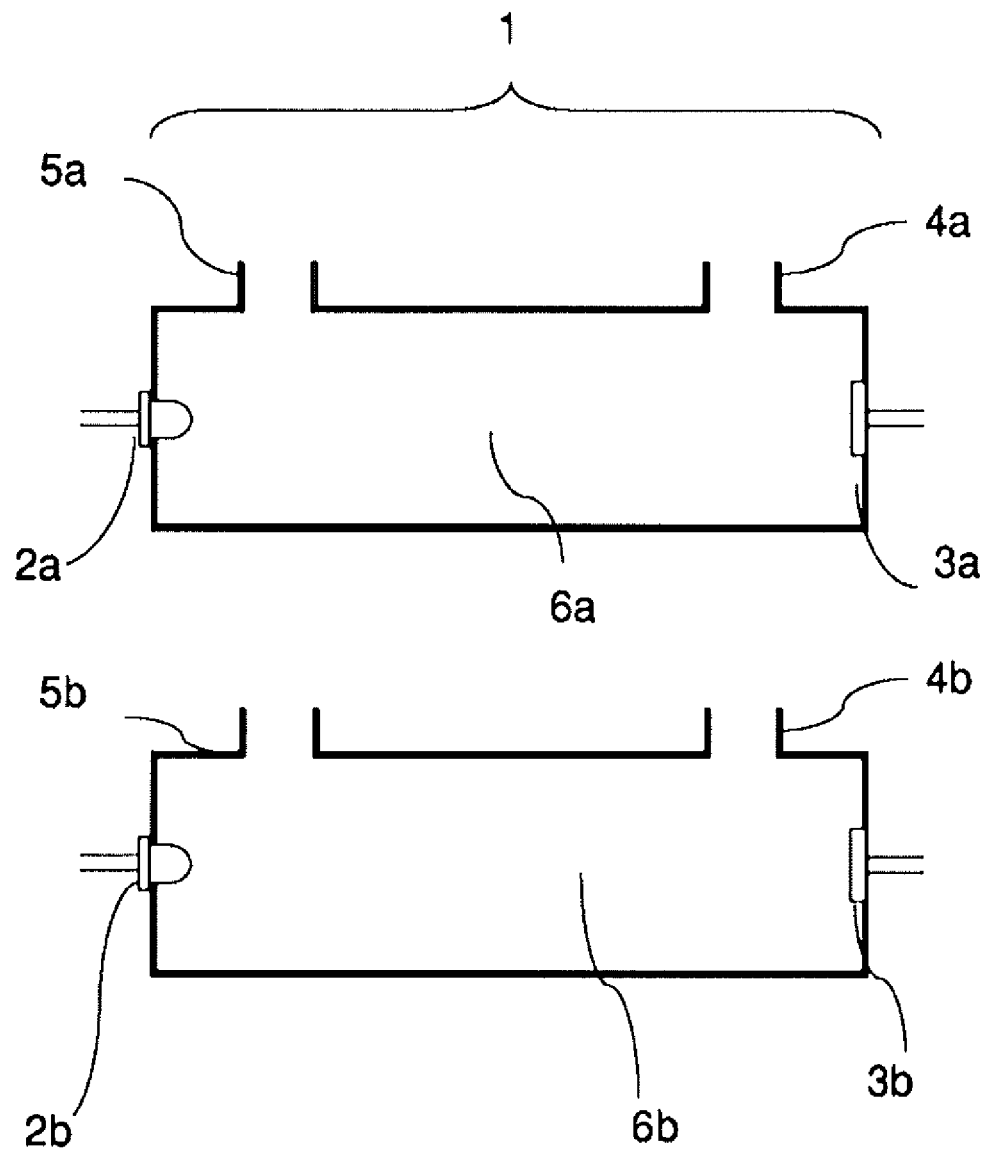
FIG. 5 depicts a chlorine dioxide sensor apparatus comprising a reference cell.

FIG. 5 depicts an embodiment of the invention wherein apparatus 1 comprises two LEDs 2, photodetectors 3, and flow paths 6. In one embodiment, the first flow path 6a is used to measure a sample of air from an environment treated with chlorine dioxide gas. In one embodiment, this first flow path 6a is used to measure chlorine dioxide gas until the level reaches a level of at least below about 20 ppm, 15 ppm, 10 ppm or 5 ppm. At such time where the level is below this concentration, the second flow path 6b is used to accurately determine the level of chlorine dioxide in a sample. In one embodiment, the second flow path 6b is capable of collecting a reference measurement and a sample measurement to accurately determine the amount or concentration of chlorine dioxide gas in a sample. The reference measurement can be collected by first filtering a sample to remove chlorine dioxide gas using, for example, an activated charcoal filter, or can be collected by measuring a sample that was not treated by chlorine dioxide.

In one embodiment of the apparatus depicted in FIG. 5, the two flow paths 6a, 6b are different lengths. In an exemplary embodiment, the first path length (used to measure the higher concentrations) is shorter than the second path length.

Figure 6:
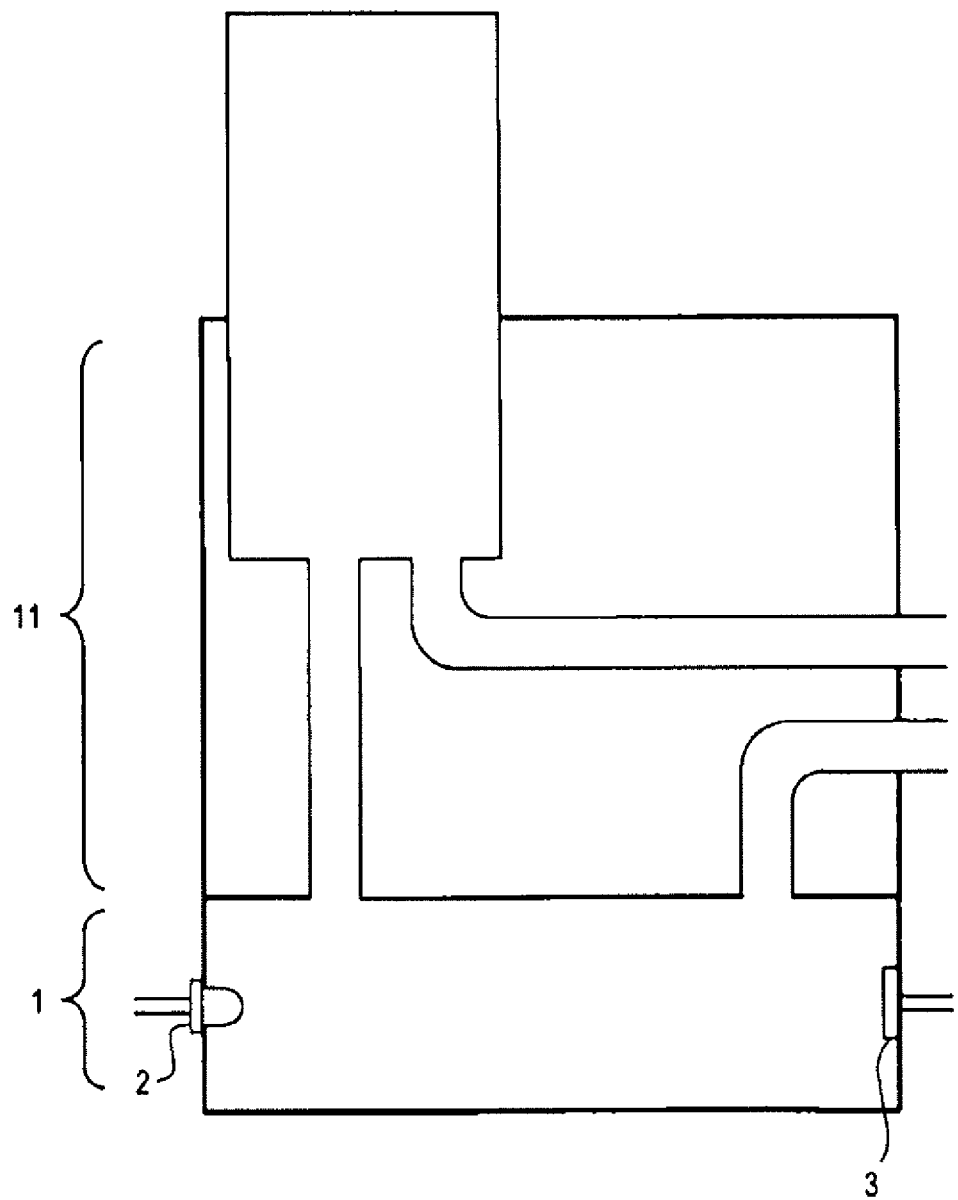
FIG. 6 depicts a chlorine dioxide sensor apparatus as part of a chlorine dioxide gas generator.

FIG. 6 depicts chlorine dioxide sensor apparatus 1 attached to chlorine dioxide generator 11.

Figure 7:
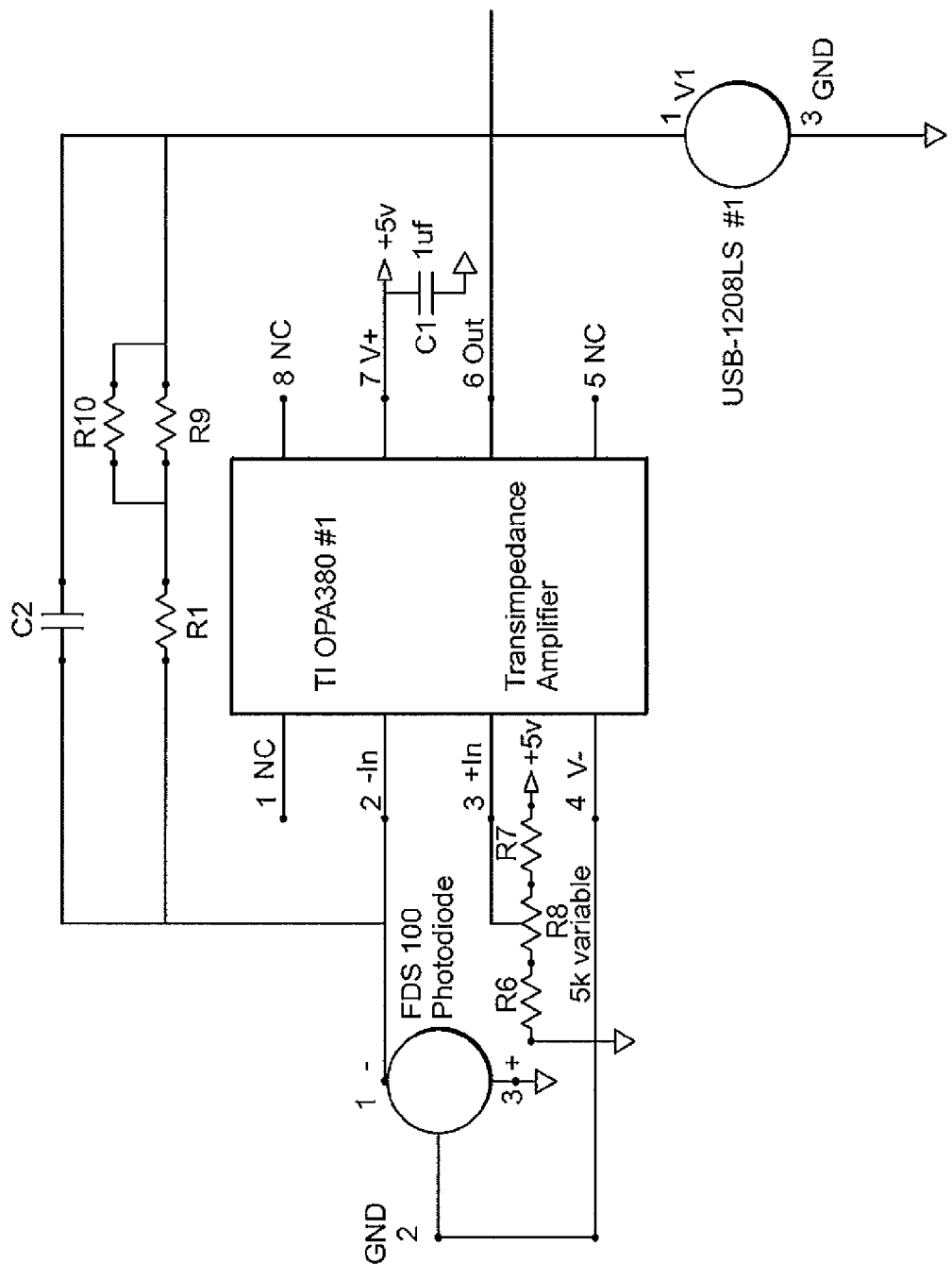
FIG. 7 is a schematic of an amplification circuit for a chlorine dioxide sensor apparatus.

FIG. 7 depicts an exemplary a schematic of an amplification circuit for a chlorine dioxide sensor apparatus.

Figure 8A:
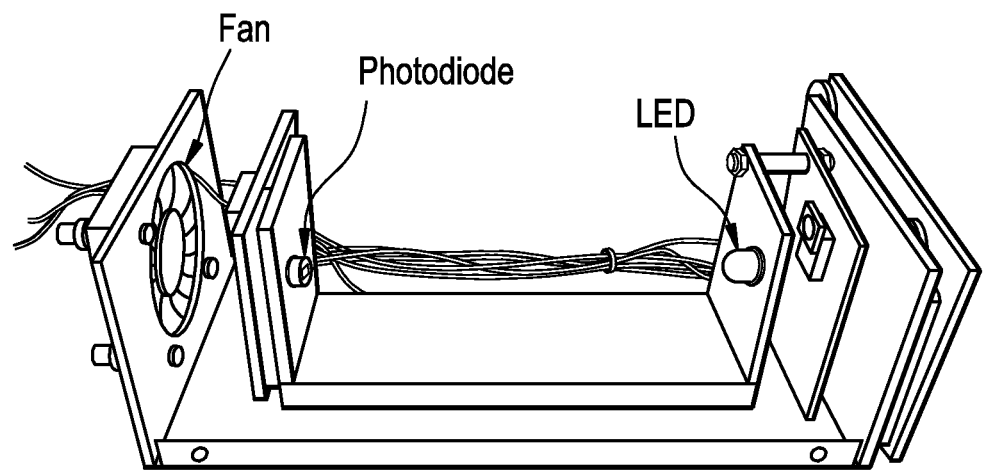
FIGS. 8A-B are pictures of a chlorine dioxide sensor apparatus of the invention.
Figure 8B:
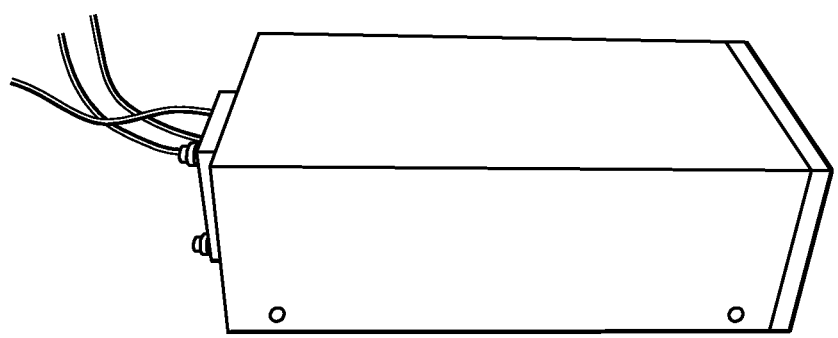

FIGS. 8A-B depicts pictures of a prototype chlorine dioxide sensor apparatus of the invention.

Figure 9:
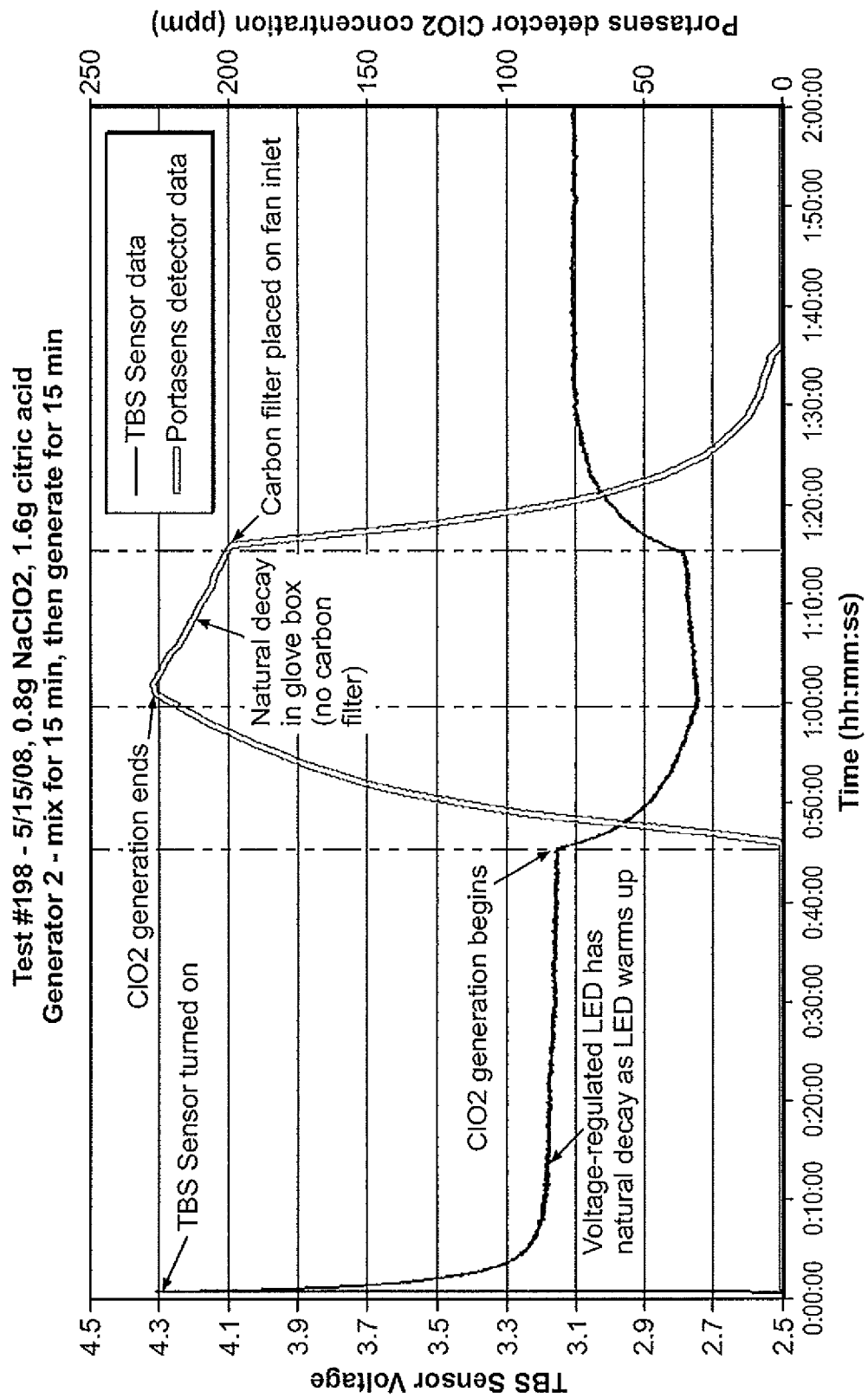
FIG. 9 is a curve of chlorine dioxide sensor apparatus data from a decontamination run in a controlled environment.

FIG. 9 is a curve of chlorine dioxide sensor apparatus data from a decontamination run in a controlled environment demonstrating the functionality of the instrument as set forth in the examples.

Figure 10:
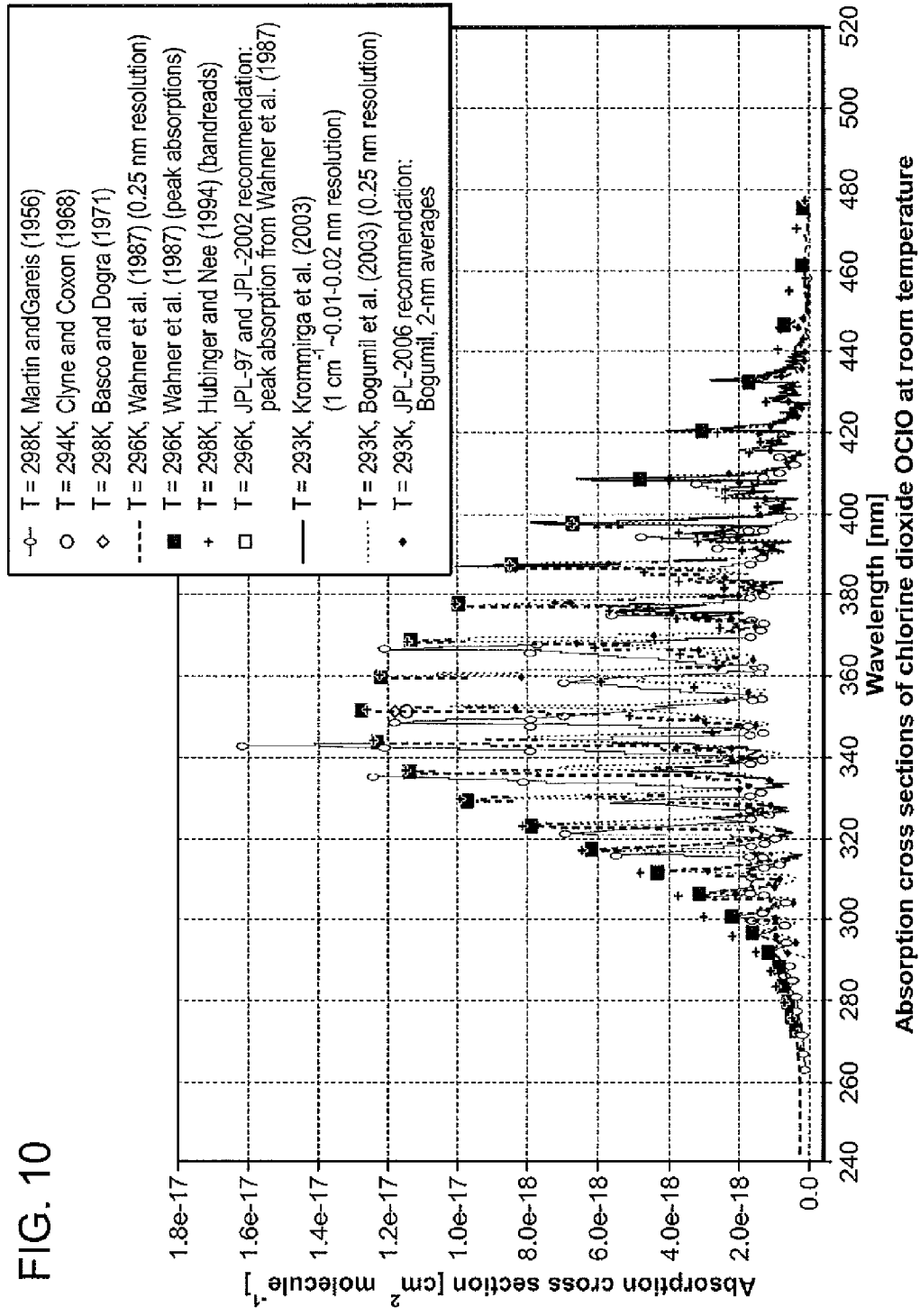
FIG. 10 depicts a compilation of extinction coefficients for $ClO_2$ at room temperature.
Figure 11:
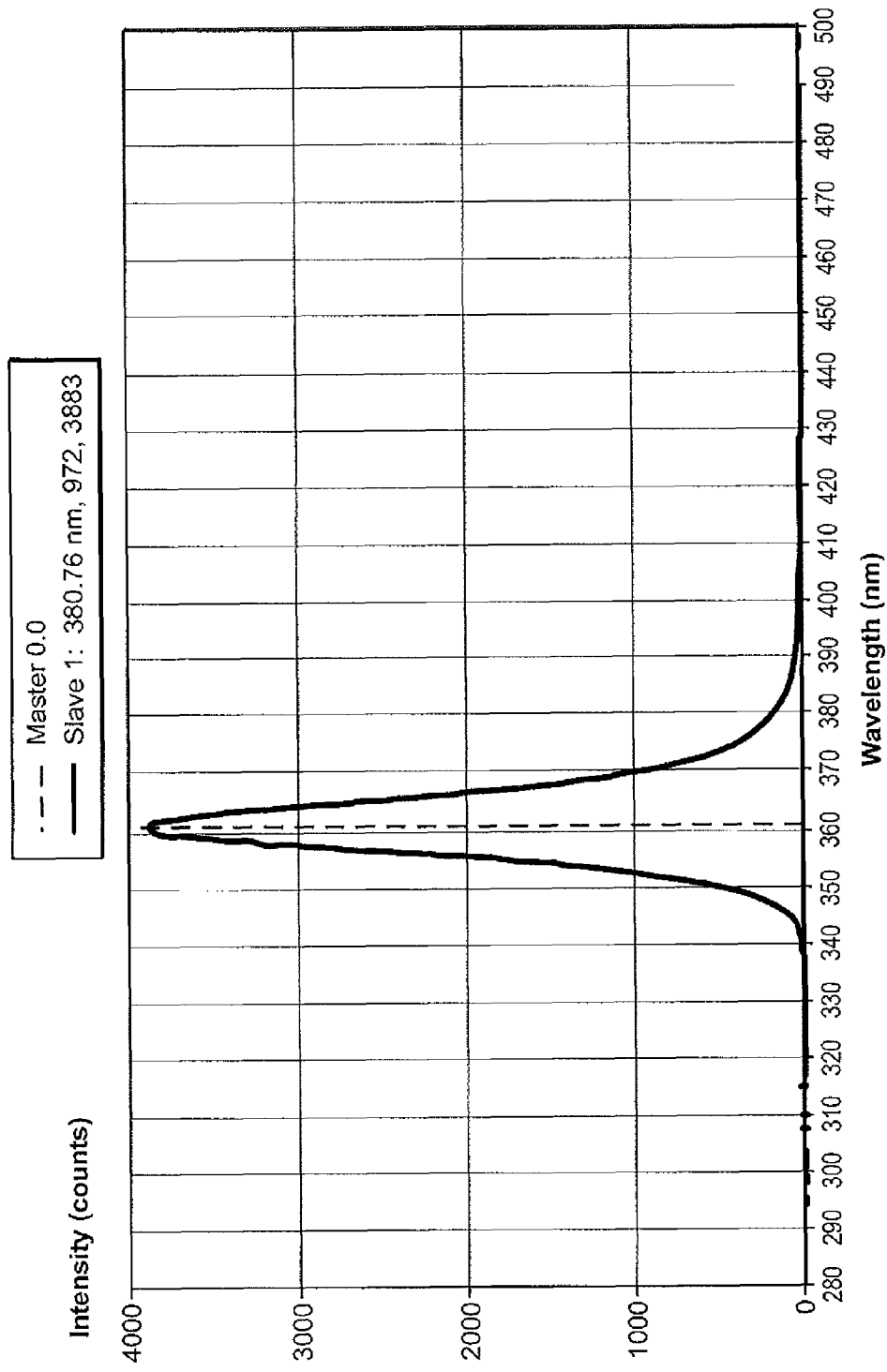
FIG. 11 depicts an exemplary spectrum from a 360 nm LED taken from the FoxUV™ 360 nm LED 5 mm.

FIG. 10 depicts a compilation of extinction coefficients for $ClO_2$ at room temperature and FIG. 11 depicts an exemplary emission spectrum from a 360 nm LED taken from a FoxUV™ LED having a 5 mm diameter and a 360 nm wavelength.

Exemplary photodetectors can be, for example, ThorLabs part number FDS100 Si Photodiode.

Chlorine dioxide has a specific absorption spectra which limits the light reaching the photodiode. The absorption spectrum of chlorine dioxide consists of a various peaks and the wavelength of the photodetector, i.e., photodiode, should be set to match a light absorbing spectral region of the sample. For example, low-cost commercially available 360 nm or 420 nm LEDs are preferred LEDs for chlorine dioxide. An exemplary LED used in the chlorine dioxide sensor apparatuses described herein can be, for example, Fox Group part number FG360-R5-WC015. The sensor will typically be in a light baffled enclosure that prevents stray light from affecting the measurement. The LED is preferably also in the enclosure. The enclosure will typically have an inlet and an outlet for the $ClO_2$ containing sample stream. Often the electronics and sensitive optics will be isolated from the $ClO_2$ containing fluid stream. If necessary, flow path isolation can be accomplished with hydrochloric acid resistant materials. If the fluid is gaseous, maintaining the critical components at a slightly elevated temperature will prevent condensation and often provide sufficient protection from corrosion. Accordingly, in specific embodiments of the invention, the apparatus comprises a thermostat and heating and/or cooling equipment to regulate the temperature of the apparatus so as to avoid condensation and/or maintain a stable operating temperature of the LED.

Selection of photodetectors that have a larger band gap can reduce the sensitivity to stray light at wavelengths longer than the energy corresponding to the band gap. An example of such a photodetector is the GaN UV enhanced diode PDU-G105A manufactured by Advanced Photonics Inc.

In a preferred embodiment, the LED 2 is driven with a current source to reduce sensor variation due to temperature and other variation because photon production in an LED is primarily proportional to current.

In a preferred embodiment, the photodiode uses a current sensing circuit to reduce sensor variation due to temperature, voltage and other variation. A voltage sensing circuit may be used, but the sensed voltage will not be linear with illumination level.

In another preferred embodiment, a reference photodiode can be used to either feedback stabilize the LED output, or to normalize the response of the sensing photodiode. Taking the ratio of the sensed total current to the reference photodiode current is a typical way to normalize the output.

In a preferred embodiment a fan or pump will be used to move a sample chlorine dioxide gas through the flow path between the light source 2 and the sensor 3.

When exposed to high energy photons (UV light, for example) chlorine dioxide in the presence of humidity can decompose and form hydrochloric acid. In a preferred embodiment, the components of the apparatus are arranged so the sample flow exits any hydrochloric acid from the sensor without passing any corrosion sensitive components.

In certain embodiments of the invention, a filter 7 is used to scrub the chlorine dioxide gas from a sample in order to obtain a reference measurement. In one embodiment, the filter 7 is an activated charcoal filter.

In another embodiment, an additional filter 15, such as a HEPA filter impregnated with sodium bicarbonate, is placed at the outlet 5 to neutralize any hydrogen chloride formed.

The path length between the LED 2 and the photodetector 3 will determine the absorption with a relatively long path length, such as 12 inches, used to sense lower concentrations and relatively short path length, such as 3 inches, to sense higher concentrations.

In one embodiment of the invention, one or more minors are used to create a long path length within a relatively small sensor enclosure by reflecting the light from the light source one or more times before the light reaches the detector. The multiple pass folded optical path is used to increase the sensitivity. The following folded optical path designs are incorporated into this document by reference: Multiple pass optical cells are used to achieve very long optical path lengths in a small volume and have been extensively used for absorption spectroscopy, (White, J. U., "Long Optical Paths of Large Aperture," J. Opt. Soc. Am., vol. 32, pp 285-288 (May 1942); Altmann, J. R. et al., "Two-mirror multipass absorption cell," Appl. Opt., vol. 20, No. 6, pp 995-999 (15 Mar. 1981) laser delay lines (Herriott, D. R., et al., "Folded Optical Delay Lines," Appl. Opt., vol. 4, No. 8, pp 883-889 (August 1965)), Raman gain cells (Trutna, W. R., et al., "Multiple-pass Raman gain cell," Appl. Opt., vol. 19, No. 2, pp 301-312 (15 Jan. 1980)), interferometers (Herriott, D. H., et al., "Off-Axis Paths in Spherical Minor Interferometers," Appl. Opt., vol. 3, No. 4, pp 523-526 (April 1964)), photoacoustic spectroscopy (Sigrist M. W., et al., "Laser spectroscopic sensing of air pollutants," Proc. SPIE, vol. 4063, pp. 17 (2000)) and other resonators (Yariv, A., "The Propagation of Rays and Spherical Waves," from Introduction to Optical Electronics, Holt, Reinhart, and Winston, Inc., New York (1971), Chap. 2, pp 18-29; Salour, M. M., "Multipass optical cavities for laser spectroscopy," Laser Focus, 50-55 (October 1977)). Cells have taken the form of White cells (White, J. U., "Long Optical Paths of Large Aperture," J. Opt. Soc. Am., vol. 32, pp 285-288 (May 1942)) and its variants (Chernin, S. M. and Barskaya. E. G., "Optical multipass matrix systems," Appl. Opt., vol. 30, No. 1, pp 51-58 (January 1991)), integrating spheres (Abdullin, R. M. et al., "Use of an integrating sphere as a multiple pass optical cell," Sov. J. Opt. Technol., vol. 55, No. 3, pp 139-141 (March 1988)), and stable resonator cavities (Yariv, A., "The Propagation of Rays and Spherical Waves," from Introduction to Optical Electronics, Holt, Reinhart, and Winston, Inc., New York (1971)).

The stable resonator is typified by the design of Herriott (Herriott, D. H., et al., "Off-Axis Paths in Spherical Minor Interferometers," Appl. Opt., vol. 3, No. 4, pp 523-526 (April 1964)). The simplest such Herriott cell consists of two spherical minors of equal focal lengths separated by a distance d less than or equal to four times the focal lengths f of the mirrors. This corresponds to stable resonator conditions. A collimated or focused laser beam is injected through the center of a hole in one of the minors, typically an off-axis location near the minor edge. The beam is periodically reflected and refocused between these mirrors and then exits through the center of the input hole (corresponding exactly to the entry position of the input beam, defining the re-entrant condition) after a designated number of passes N, in a direction (slope) that is different from the entry slope. As a result, the total optical path traversed in the cell is approximately Nd. The pattern of reflected spots observed on the mirrors in these cells forms an ellipse. Re-entrant conditions for spherical mirror Herriott cells are restricted by certain predetermined ratios of the mirror separation d to the focal length f and the location and slope of the input beam. For any re-entrant number of passes N, all allowed solutions are characterized by a single integer M. Excellent descriptions for the design, setup and use of these cells are given by Altmann (Altmann, J. R., et al., "Two-mirror multipass absorption cell," Appl. Opt., vol. 20, No. 6, pp 995-999 (15 Mar. 1981) and McManus (McManus, J. B., et al., "Narrow optical interference fringes for certain setup conditions in multipass absorption cells of the Herriott type," Appl. Opt., vol. 29, No. 7, pp 898-900 (1 Mar. 1990)).

When the cell volume must be minimized relative to the optical path length or where a very long optical path (>50 m) or very small footprint is desired, it is useful to increase the density of passes per unit volume of cell. The conventional spherical mirror Herriott cell is limited by the number of spots one can fit along the path of the ellipse without the spot adjacent to the output hole being clipped by or exiting that hole at a pass number less than N. This approximately restricts the total number of passes to the circumference of the ellipse divided by the hole diameter, which in turn is limited by the laser beam diameter. For a 25-mm radius mirror with a relatively small 3-mm diameter input hole located 20 mm from the center of the mirror, a maximum of about $$\frac{2\pi 20}{3} \approx 40,$$

or 80 passes is possible at best. Generally, the hole is made larger to prevent any clipping of the laser input beam that might lead to undesirable interference fringes, and typical spherical Herriott cells employ less than 60 passes.

Herriott (Herriott, D. R. and Schulte, H. J., "Folded Optical Delay Lines," Appl. Opt., vol. 4, No. 8, pp 883-889 (August 1965)) demonstrated that the use of a pair of astigmatic mirrors could greatly increase the spot density, and hence optical path length, in the cell. Each mirror has different finite focal lengths ($f_x$ and $f_y$) along orthogonal x and y axes, and the mirrors are aligned with the same focal lengths parallel to one another. The resulting spots of each reflection on the mirrors create precessions of ellipses to form Lissajous patterns. Since these patterns are distributed about the entire face of each mirror, many more spots can be accommodated as compared to a cell with spherical mirrors. Herriott defines the method of creating the astigmatic mirror as distortion of a spherical mirror, either in manufacture or in use, by squeezing a spherical mirror in its mount. He states that the amount of astigmatism required is very small and amounts to only a few wavelengths. McManus (McManus, et al., "Astigmatic mirror multipass absorption cells for Ion-path-length spectroscopy," Appl. Opt., vol. 34, No. 18, pp 3336-3348 (20 June 1995)) outlines the theory and behavior of this astigmatic Herriott cell and shows that the density of passes can be increased by factors of three or more over spherical mirror cells. For these astigmatic mirror cells, light is injected through a hole in the center of the input mirror. Allowed solutions for re-entrant configurations are characterized by a pair of integer indices $M_x$ and $M_y$, since there are now two focal lengths present along orthogonal axes.

Chlorine dioxide has a UV extinction coefficient which varies rapidly with wavelength as depicted in FIG. 10. Beers Law states that the relationship between light attenuation and concentration will be logarithmic. Beers Law is applicable only to absorbance over bandwidths sufficiently narrow to contain essentially a single extinction coefficient. In one embodiment of the invention using a light source which covers a wavelength range that is broad compared to the extinction coefficient fine structure, the light level and path length are set to have a small percentage loss of light so the light attenuation is nearly linearly proportional to the sample concentration. The path length is chosen to preferably contain less than 50%, more preferably less than 30%, and still more preferably less than 10% extinction of light at the peak absorbance wavelength incorporated in the measurement.

In another embodiment of the invention, using multiples optical passes, the number of passes is changed during the measurement to vary the path length. The absorbance is calculated from at least two different path lengths according to Beers law and the divergence from Beers law is used to determine the level of $ClO_2$. Adsorption and scattering losses due to mirror surface contamination as well as scattering losses from the sample stream are broad spectrum and will be relatively wavelength independent over any portion of the wavelength range between 300 to 440 nanometers, and therefore will adhere to Beers law. The light loss from the spectral fine structure of the extinction coefficient will not follow Beers law, but is calculated by integrating the Beers law result for each narrow bandwidth slice of the spectrum using the specific light intensities and the corresponding extinction coefficients. See FIG. 11 for a typical light intensity vs. wavelength for a suitable LED.

In another embodiment of the invention, one or more curved mirrors are used to focus the light on the detector.

In another embodiment of the invention, lenses are used to focus the light source on the detector to get a larger signal from the sample.

In another embodiment of the invention, a reference signal is used.

In another embodiment of the invention, the sensor is run without a sample at the beginning of each use cycle to determine a reference signal.

In another embodiment of the invention, one or more path lengths are used simultaneously. In this way, low concentrations, such as 0.1 to 0.3 ppm, can be measured accurately as well as high concentrations, such as 500-2000 ppm, in the same sensor. Typically there is a large range between decontamination concentrations and safe gas levels, so it is useful to measure both low levels for safety and high levels for dosing.

In a further embodiment of the invention, the short path signal may be used as a reference signal for low concentrations. At high concentrations, the short path signal is used with the reference signal being saved from before introduction of the ClO2. In another embodiment of the invention the sensor electronics uses two gain stages to measure high and low concentrations of the sample.

In another embodiment, a movable mirror is used to vary the path length from short to long with a single light source and sensor. Comparison of the two signals from the short and long path lengths can be used to make a sensor with two accurate ranges that are several orders of magnitude apart.

In another embodiment of the invention, the sensor output is recorded, for example by a digital data acquisition system, for later review. The output may include other relevant information such as the test date, decontamination protocol, equipment code, temperature, humidity, etc.

In another embodiment of the sensor, the sample stream is repeatedly alternated with a reference stream that is free of the $ClO_2$. This compensates for optical surface contamination as well as light source and detector changes that may take place over the monitoring time. In one version of this embodiment, the reference stream is derived from the sample stream by passing the sample stream through a scrubbing filter 7, such as activated carbon, preferably with a high surface area.

In another embodiment of the sensor alternating a sample stream with a reference stream, a ClO$_2$ scrubber such as an activated carbon filter is placed on the exhaust of the sensor. The reference stream is obtained by reversing the direction of flow through the sensor, so the stream passes through the scrubber before entering the sensor.

In another embodiment of the sensor alternating a sample stream with a reference stream, the reference stream is obtained from a source independent of the ClO$_2$ treatment zone. A specific embodiment related to measurement and control of ClO$_2$ levels inside an enclosed treatment space such as a bio-safety cabinet, the reference gas stream is obtained from outside the treatment space.

In another embodiment of the invention the sensor include wireless communication to a recorder or readout. Being able to place sensors throughout an environment to be decontaminated is desirable. For example, placing a sensor above the HEPA filter in a biosafety cabinet will allow confirmation that the required dose of disinfectant was delivered in a hard to reach location.

The instant invention provides apparatus and methods for sensing and delivering chlorine dioxide.

In one embodiment of the invention, a chlorine dioxide generator is placed inside a controlled environment to be decontaminated.

In one embodiment of the invention, a chlorine dioxide generator is connected to a controlled environment through one or more ports.

In one embodiment of the invention, a chlorine dioxide generator is connected to a controlled environment through in inlet and outlet port.

In another embodiment of the invention, the chlorine dioxide generator has a sensor.

In another embodiment of the invention, the sensor feeds back information about the chlorine dioxide concentration and adjusts the output of the generator to control the dose profile, concentration vs. time, for the decontamination.

In another embodiment of the invention, a pressure sensor is used to check the controlled environment for leak rate either at the beginning of the process or continuously during the process.

In another embodiment, a pump or fan is used to maintain the controlled environment at a negative pressure so chlorine dioxide does not escape the controlled environment. In another embodiment the flow rate passing through this pump or fan, as well as the differential pressure is monitored.

In another embodiment, a filter 15, for example an activated carbon filter, is used at the outlet to adsorb some of the chlorine dioxide exiting the controlled environment.

In another embodiment, a filter 15, for example an activated carbon filter, is used at the outlet to adsorb some of the chlorine dioxide exiting the controlled environment so the exiting flow is below a safety limit (0.3 or 0.1 ppm, for example) for chlorine dioxide.

In another embodiment, a humidity and temperature sensor is used to ensure that water vapor is not condensing inside the controlled environment.

In another embodiment, a humidification means is used to control the humidity in the controlled environment. High humidity, for example 70-95% RH, has been shown to increase bacterial spores' susceptibility to chlorine dioxide.

In another embodiment, a dehumidification means is used remove liquid water from the controlled environment.

In another embodiment, two or more sensors are used as a safety check.

In another embodiment, two or more sensors are used where the sensors are place to measure concentration in different parts of the controlled environment to measure the dose to that area.

The various combinations of the above embodiments are intended to be within the scope of the instant invention.

EXAMPLE 1

Chlorine dioxide gas was generated by a chlorine dioxide generator and a sensor apparatus of the invention was used to measure the concentration of chlorine dioxide in the treated environment. The results of this experiment are presented in FIG. 9.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the instant invention and the following claims.

What is claimed is:

1. An apparatus for measuring a concentration of a chlorine dioxide gas in a sample, the apparatus comprising,
    a light emitting diode (LED),
    a light sensor, and
    a flow path between the LED and the light sensor, the flow path capable of containing a sample; and
    a filter configured to remove chlorine dioxide from a reference stream;
    wherein the sensor is capable of measuring the level of chlorine dioxide in the sample and the reference stream.

2. The apparatus of claim 1, further comprising a second light sensor.

3. The apparatus of claim 1, wherein the sensor and the LED are thermostated.

4. The apparatus of claim 1, wherein the apparatus is heated.

5. The apparatus of claim 1, further comprising an air moving device.

6. The apparatus of claim 1, wherein the filter is an activated carbon filter.

7. The apparatus of claim 1, further comprising a second filter at the outlet.

8. The apparatus of claim 7, wherein the second filter is suitable for neutralizing acids.

9. The apparatus of claim 7, wherein the second filter is suitable for neutralizing hydrogen chloride gas.

10. The apparatus of claim 1, wherein the path between the sensor and the detector includes one or more optical elements for focusing the light source on the light sensor.

11. The apparatus of claim 10, wherein the optical elements include one or more lenses for focusing the light on the detector.

12. The apparatus of claim 1, further comprising two or more optical paths within the flow path, the optical paths used for sensing different concentration levels or for reference measurements.

13. The apparatus of claim 1, further comprising a wireless connection to a recorder or display.

14. The apparatus of claim 1, further comprising a chlorine dioxide generating apparatus.

15. The apparatus of claim 1, further comprising a valve configured to alternatively admit the sample or the reference stream into the flow path.

16. The apparatus of claim 1, wherein the reference stream is obtained from the same source as the sample.

* * * * *